US006545040B1

(12) United States Patent
Xhonneux et al.

(10) Patent No.: US 6,545,040 B1
(45) Date of Patent: Apr. 8, 2003

(54) METHOD OF LOWERING THE BLOOD PRESSURE

(75) Inventors: Raymond Mathieu Xhonneux, Vlimmeren (BE); Guy Rosalia Eugène Van Lommen, Berlaar (BE)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 07/825,488

(22) Filed: Jan. 24, 1992

Related U.S. Application Data

(63) Continuation of application No. 07/325,181, filed on Mar. 16, 1989, now abandoned, which is a continuation-in-part of application No. 07/172,747, filed on Mar. 23, 1988, now abandoned.

(51) Int. Cl.$^7$ ...................... A61K 31/35; A61K 31/335; A61K 31/18
(52) U.S. Cl. ......................... 514/451; 514/452; 514/602
(58) Field of Search ................................. 514/451, 452, 514/602

(56) References Cited

U.S. PATENT DOCUMENTS 4,654,362 A    3/1987  Van Lommen et al. ...... 514/452

OTHER PUBLICATIONS

Van de Water et al. 109 CA:16771g 1988.*
Van de Water 110 CA:50943v 1988.*
Kakoki, M., et al. Effects of Vasodilatoryβ–Adrenoceptor Antagonists on Endothelium–Derived Nitric Oxide Release in Rat Kidney. Hyptertension, 1999, 33 [part II] 467–471.
LaCourcière, Y. et al., Comparative Assessment of Antihypertensive Efficacy of DL–Nebivolol and D–Nebivolol in Patients with Confirmed Mild to Moderate Hypertension, Journal of Cardiovascular Pharmacology, 25:619–624, 1995, Raven Press, Ltd., New York.
Parenti, A., et al., Inositol Phosphate Metabolism and Nitric–Oxide Synthase Activity in Endothelial Cells Are Involved in the Vasorelaxant Activity of Nebivolol. J. Pharmacology and Experimental Therapeutics, 292:698–703 (2000).
Pauwels, P.J., et al., The Receptor Binding Profile of the New Antihypertensive Agent Nebivolol and Its Stereoisomers Compared with Various β–Adrenergic Blockers, Molecular Pharmacology, 34:843–851, 1988.
Pouleur, M.D., Effects of d–nebivolol and l–nebivolol on Left Ventricular Systolic and Diastolic Function, Janssen Research Foundation, NEB–BEL–41, 1991.
Ritter, J., et al., A Study to Investigate the Vasodilator Effect of fNebivolol Racemate & Isomers on Forearm Blood Flow in Healthy Volunteers, JRF, Clinical Research Report, Trial NEB–GBR–31, Jul. 1997.
Ritter, J., et al., A Study to Investigate the Possible Vasodilator Effect of Nebivolol on Forearm Blood Flow in Healthy Volunteers, NEB–GBR–23, Aug. 16, 1992—Aug. 27, 1992.
Ritter, J.M., A Study to Investigate the Mechanism of the Vasodilator Effect of Nebivolol Isomers on Forearm Blood Flow in Healthy Volunteers, JRD, Clinical Research Report, NEB–GBR–29, N106922, 1994.
Ritter, J.M., et al., A Study to Investigate the Vasodilator Action of Nebivolol in Patient Volunteers with Essential Hypertension, JRF Clinical Research Report, Jan. 1998.
Ritter, J.M., et al., A Study to Compare the Effect of Nebivolol and Atenolol on Forearm Blood Flow in Healthy Volunteers, JRF, Clinical Research Report on NEB–GBR–27, (N 107424), Oct. 1993.
Robertson, J.I.S., Janssen Research Foundation, Clinical Expert Report, Jan. 1995, 1–47.
Rousseau, M.F. et al., Perfusion 10/97, p. 367–375.
Rousseau, M.F., et al., Long–term Effects of Nebivolol on Ischaemic Left Ventricular Dysfunction, Janssen Research Foundation, Oct. 1994.
Rousseau, M.F., et al., Medium–term Effects of Beta–blockade on Left Ventricular Mechanics: A Double–blind, Placebo–controlled Comparison of Nebivolol and Atenolol in Patients wit Ischemic Left Ventricular Dysfunction, Journal of Cardiac Failure, vol. 2, No. 1, 1996.
Stoleru, L. et al., Effects of d–Nebivolol and L–Nebivolol on Left Ventricular Systolic and Diastolic Function: Comparison with D–L–Nebivolol and Atenolol, Journal of Cardiovascular Pharmacology, 22:183–190, 1993, Raven Press, Ltd., New York.
Stoleru, L., et al., Beneficial Effect of (d–I) Nebivolol on the Left Ventricular Systolic and Diastolic Function, European Heart Journal 13 (Suppl.), p. 21, 1992.
Van de Water, A., et al., Cardiovascular Effects of dl–nebivolol and its enantiomers—a Comparison with Those of Atenolol, Eur. J. Pharmacol, 1988 Abstract.
Van de Water, A., et al., Pharmacological and Hemodynamic Profile of Nebivolol, A Chemmically Novel, Potent, and Selective β1–adrenergic Antagonist, J. Cardiovasc. Pharmacol, 1988 Abstract.
Van de Water, A., et al., The Cardiac and Haemodynamic Effects of Cumulative Intravenous Injections of R 65 825 in Closed–Chest Anaesthetized Mongrel Dogs, Janssen Research Products Information Service, Mar. 1985.

(List continued on next page.)

Primary Examiner—Russell Travers

(57) ABSTRACT

A method of potentiating the effects of blood pressure reducing agents in warm-blooded animals, said method comprising administering to said warm-blooded animals of an effective amount of a blood pressure reducing agent and a 2,2'-iminobisethanol derivative.

6 Claims, No Drawings

OTHER PUBLICATIONS

Van de Water, A., et al., The Cardiac and Haemodynamic Effects of Intravenous Injections of R 65 824 in Closed–Chest Anaesthetized Mongrel Dogs, Janssen Research Products Information Service, R 65 824/1, Apr. 1985.

Van de Water, A., et al., The Comparison of the Cardiac and Haemodynamic Effects of Cumulative Intravenous Injections of R 65 824 and Those of R 65 825 with Those of Propranolol in Closed–Chest Anaesthetized Mongrel Dogs, Janssen Research Products Information Service, R 65 824/3, R 65 825/3, Jul. 1985.

Van de Water, A., et al., The In Vivo Beta–Adrenergic Blocking Properties of an Intravenous Administration of R 65 825 in Closed–Chest Anaesthetized Mongrel Dogs, Janssen Research Products Information Service, R 65 825/2, Mar. 1985.

Van de Water, A., et al., The In Vivo Beta–Adrenergic Blocking Properties of an Intravenous Administration of R 65 824 in Closed–Chest Anaesthetized Mongrel Dogs, Janssen Research Products Information Service, R 65 824/2, May 1985.

Van Nueten, J.M., et al., In Vitro Pharmacological Profile of R 65 824, A Potent and Selective β1–adrenergic Antagonist, Janssen Research Products Information Service, Nov. 1985.

Van Nueten, L. et al., Nebivolol: Comparison of the Effects of dl–Nebivolol, d–Nebivolol, l–Nebivolol, Atenolol, and Placebo on Exercise–Induced Increases in Heart Rate and Systolic Blood Pressure, Cardiovascular Drugs and Therapy, 1998, 12:339–344, Kluwer Academic Publisher, Boston.

Van Rooy, P, Determination of the Acute and Subacute β–sympthiocolytic Activity of d–, l–and dl–nebivolol Compared to Atenolol and Placebo, in Inhibiting Exercise–Induced Tachycardia, NEB–BEL–20, Janssen Research Foundation, 1989.

Wisenbaugh, Thomas MD, et al., Long–Term (3–month) Effects of a New Beta–Blocker (Nebivolol) on Cardiac Performance in Dilated Cardiomyopathy, JACC, vol. 21, No. 5, Apr. 1993:1094–1100.

Xhonneux, R., et al., The l–enantiomer of Nebivolol Potentiates the Blood Pressure Lowering Effect of the d–enantiomer, European Journal of Pharmacology, 181, 1990, 261–265, Elsevier Science Publishers.

Bowman, A.J. et al., Nitric Oxide Mediated Venodilator Effects of Nebivolol, Br J Clin Pharmacology, 1994, 38: 199–204.

Cockcroft, J.R., et al., Effect of Racemic Nebivolol on Forearm Blood Flow in Healthy Volunteers, British Journal of clinical Pharmacology 35 (5) p. 542p–543p, 1993.

Cockcroft, J.R., et al., Nebivolol Causes Vasodilation in Human Forearm Vasculature: Evidence for an L–arginine/no Dependent MechanismAmerican Journal of Hypertension 7 (4) Part 2, 1183, p. 23A, 1994.

Cockcroft, J.R., et al., Nebivolol Induced Vasodilation in the Human Forearm May be Mediated by the L–ARG/NO Pathway, Third International Meeting on the Biology of Nitric Oxide, Cologne, Germany, Oct. 3–6, 1993.

Cockcroft, J.R., et al., Perfusion 11/97, p. 414–420.

Crockcroft, J.R., et al., Nebivolol Vasodilates Human Forearm Vasculature: Evidence for an–l–Arginine/NO–Dependent Mechanism, The Journal of Pharmacology and Experimental Therapeutics, 1995, 274:1067–1071.

Dawes, M., et al., The Vasodilator Action of Nebivolol in Forearm Vasculature of Subjects with Essential Hypertension, Br. J. Clinical Pharmacology 48, 460–463, 1999.

De Crée, J. et al., Non–invasive Cardiac Haemodynamics of Nebivolol in Men, Acta Antwerpiensá 6 (2), 1989.

De Cree, J., Comparison of the Hemodynamic Effects of Nebivolol and Atenolol, JRF, clinical Research Report 33, Jan. 1989 (N 65577) 6:2–21.

De Cree, J., et al., Cardiac Haemodynamic Effects of d–, l–, dl–nebivolol and Atenolol During a 7–day Double–blind Cross–over Study in Healthy Volunteers, Janssen Research Products Information Services, Clinical Research Report, Mar. 1989.

De Cree, J., et al., Double–blind Fplacebo–controlled Cross– over Study Evaluating the Acute Haemodynamic Effects of dl–nebivolol 5 mg, d–nebivolol 2.5 mg and l–nebivolol 2.5 mg in Healthy Volunteers, Janssen Research Products Information Services, Clinical Research Report, Feb. 1989.

De Cree, J., et al., Double–blind Study Comparing the Subacute Hemodynamic Effects in Men at Rest and During Exercise of the 2 Enantiomers of dl–nebivolol, d–nebivolol (R 67138) and l–nebivolol (R 67145), Janssen Research Products Information Service, Clinical Research Report, Mar. 1988.

De Cree, J., et al., Effects of Isometric Handgrip on Blood Pressure and Heart Rate During a 7–day Double–Blind Cross–over Treatment with dl–, d–and l–nebivolol and Atenolol, Janssen Research Products Information Services, Clinical Research Report, Jan. 1989.

E. Snook et al., JRF, Comparative Pharmacokinetics of Nebivolol after a Single Oral Dose of 7.5mg d–nebivolol, 7.5 mg l–nevivolol and 15 mg of the Racemate Nebivolol in 4 Extensive and 2 Poor Metabolisers of Debrisoquine, NEB–BEL–22, Oct. 1994.

G. Cheymol et al., Pharmacokinetic Study and Cardiovascular Monitoring of Nebivolol in Normal and Obese Subjects, Eur. J. Clin. Pharmacol, 1997, 51:493–498.

Gao, Y., et al., Nebivolol Induces Endothelium–Dependent relaxations of Canine Coronary Arteries, Journal of Cardiovascular Pharmacology, 17:964–969, 1991, Raven Press, Ltd., New York.

Goldstein, M. et al., Administration of Nebivolol after Coronary Artery Bypass in Patients with Altered Left Ventricular Function, Journal of Cardiovascular Pharmacology, 22:253–258, 1993, Raven Press, Ltd., New York.

Himmelmann, A. et al., Haemodynamic Effects and Pharmacokinetics of Oral d–and l–nebivolol in Hypertensive Patients, Eur, J. Clin Pharmacol, 1996, 51: 259–264.

JRF, A Study to Investigate the Mechanism of the Vasodilator Effect of Nebvivolol on Forearm Blood Flow in Healthy Volunteers, NEB–GBR–25, 1993, Ritter.

JRF, A Study to Investigate the Mechanism of the Vasodilator Effect of Nebivolol on Forearm Blood Flow in Healthy Volunteers, NEB–GBR–28, 1993, Ritter.

JRF, Double–blind, Placebo–controlled Phase–II Study of di–Nebivolol and its d–and l–enantiomers in Patients With Mild to Moderate Hypertension, Clinical Research Report NEB–GER–9, I 1993 (N 106 599).

JRF, Effect of Nebivolol and its Enantiomers in Hypertensive Patients, Comparison with Placebo and Atenolol, Clinical Research Report NEB–INT–4, Jun. 1993 (N 92909).

JRF, Synoptic Clinical Research Report NEB–BEL–26, Sep. 1994, De Meirleir.

JRF, Synoptic Clinical Research Report NEB–BEL–42, Jan. 1994 (N 106563), Goldstein.

* cited by examiner

METHOD OF LOWERING THE BLOOD PRESSURE

CROSS-REFERENCE TO RELATED APPLICATIONS

This application is a continuation of our application Ser. No. 07/325,181, filed on Mar. 16, 1989, (now abandoned) which in turn was a continuation-in-part of application Ser. No. 07/172,747, filed on Mar. 23, 1988 now abandoned.

BACKGROUND OF THE INVENTION

In U.S. Pat. No. 4,654,362 there are described 2,2'-iminobisethanol derivatives having β adrenergic blocking properties. It now has been found that a certain class of isomers of said bisethanol derivatives potentiate the activity of blood pressure reducing agents.

DESCRIPTION OF THE INVENTION

The present invention is concerned with a group of compounds capable of potentiating the effects of blood pressure reducing agents, said compounds being represented by the formula

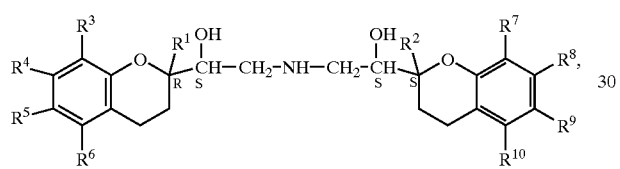

(I)

or the pharmaceutically acceptable acid addition salts thereof, wherein $R^1$ and $R^2$ each independently are hydrogen or $C_{1-6}$alkyl;

$R^3$, $R^4$, $R^5$, $R^6$, $R^7$, $R^8$, $R^9$ and $R^{10}$ each independently are hydrogen, halo, $C_{1-6}$alkyl, $C_{1-6}$alkyloxy, hydroxy, cyano, carboxy or $C_{1-6}$alkyloxycarbonyl; or two vicinal radicals of $R^3$, $R^4$, $R^5$, $R^6$, $R^7$, $R^8$, $R^9$ and $R^{10}$ taken together may form a —CH=CH—CH=CH— or —(CH$_2$)$_4$— radical.

As used in the foregoing definitions the term halo is generic to fluoro, chloro, bromo and iodo; the term "$C_{1-6}$alkyl" defines straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like.

The descriptors R and S as used in the above formula (I) indicate the absolute configuration at the respective carbon atoms. The carbon atom bearing $R^1$ has the R configuration, whereas the carbon atoms bearing the hydroxy functions and the carbon atoms bearing $R^2$ have the S configuration.

Preferred compounds of formula (I) are those wherein $R^3$, $R^4$, $R^6$, $R^7$, $R^8$, and $R^{10}$ are hydrogen.

Particularly preferred are those preferred compounds wherein $R^5$ and $R^9$ are hydrogen or halo, particularly fluoro.

The most preferred compound is [2R,αS,2'S,αS]-α,α'-[iminobismethylene]bis[6-fluoro-3,4-dihydro-2H-1-benzopyran-2-methanol] or a pharmaceutically acceptable acid addition salt thereof.

The compounds of formula (I) can be prepared following the procedures described in U.S. Pat. No. 4,654,362. Some particular ways of obtaining the compounds of formula (I) will be described hereinafter in some more detail.

The compounds of formula (I) can be prepared by reacting an oxirane of formula (II-a) or (II-b) with an amine of formula (III-a) or (III-b).

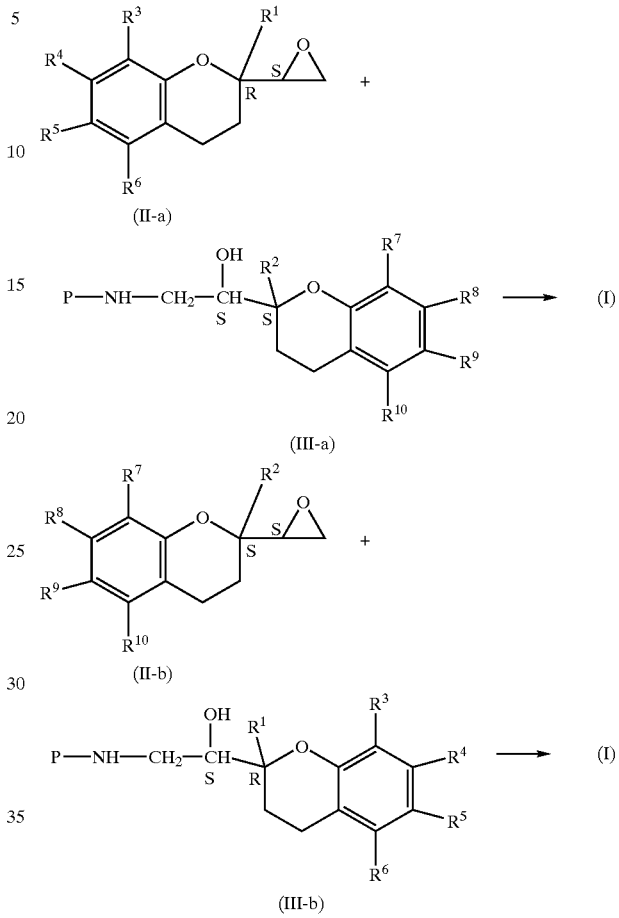

In (III-a) and (III-b), P is either hydrogen or an appropriate protecting group, for example an allyl group, or in particular P may be a benzyl group. Or, a reagent P—NH$_2$ may be reacted with (II-a) and (II-b) in a one-pot procedure. The above described reactions to prepare a compound of formula (I) may be conducted in a reaction-inert solvent such as, for example, an aromatic hydrocarbon, e.g. benzene or methylbenzene; an alkanol, e.g. methanol, ethanol, propanol; a ketone, e.g. 2-propanone, 4-methyl-2-pentanone; an ether, e.g. 1,4-dioxane, tetrahydrofuran, 1,1'-oxybisethane; a dipolar aprotic solvent, e.g. N,N-dimethylformamide or N,N-dimethylacetamide and the like solvents. In certain instances, in order to increase the reaction rate, it may be appropriate to heat the reaction mixture.

If in the above reactions P is other than hydrogen, the N-protected derivatives of formula (I) are obtained wherefrom the compounds of formula (I) themselves can be obtained by a deprotection reaction. For example, where P is allyl, by reaction with an appropriate noble metal compound such as PdCl$_2$ or Rh[P(C$_6$H$_5$)$_3$]Cl, or where P is benzyl, by a catalytic hydrogenation procedure, e.g. palladium or platinum on charcoal in a suitable solvent such as an ether, e.g. 1,4-dioxane, tetrahydrofuran, an alkanol, e.g. methanol, ethanol, an alkoxyalkanol, e.g. methoxyethanol and the like.

The intermediates of formula (II-a) or (III-b) are obtained by the reaction of the amine P-KH$_2$ with (II-b) or (II-a) or, by reacting a reagent P$_2$NH, for example dibenzylamine, with (II-b) or (II-a) and subsequently selectively removing one of the P-groups, e.g. when P is benzyl by a catalytic hydrogenation procedure using one equivalent hydrogen. The afore described reactions to prepare (III-a) or (III-b) are conducted following the same procedures as described hereinabove for the preparation of the compounds (I).

The starting materials (II-a) are obtained by an oxirane formation reaction from an aldehyde of formula (IV-a), e.g. by reaction of the latter with a trimethylsulfoxonium halide, or from an ethylene of formula (V-a) by reaction of the latter with a peroxide, e.g. a haloperbenzoic acid. In the same way, the intermediate (II-b) is obtained from the corresponding S-isomers (IV-b) or (V-b). The oxiranes of formula (IV-a-1) obtained in the aforementioned oxirane-formation reaction are separated in their stereoisomers, e.g. by HPLC or selective crystallization.

The compounds of formula (I) with the exception of (RSSS)-α,α'-[iminobis(methylene)bis(3,4-dihydro-2H-1-benzopyran-2-methanol] ethanedioate(1:1) are deemed to be novel compounds and constitute in an additional feature to the present invention.

The compounds of formula (I) and the pharmaceutically acceptable acid addition salts thereof potentiate the activity of blood pressure reducing agents. In particular they potentiate the reduction of the blood pressure and of the heart rate.

As blood pressure reducing agents of which the activity is potentiated there may be mentioned agents having adrenergic and/or vasodilating activity. In particular such agents may be the compounds mentioned in U.S. Pat. Nos. 3,663,607 and 3,836,671, in particular atenolol; U.S. Pat. Nos.

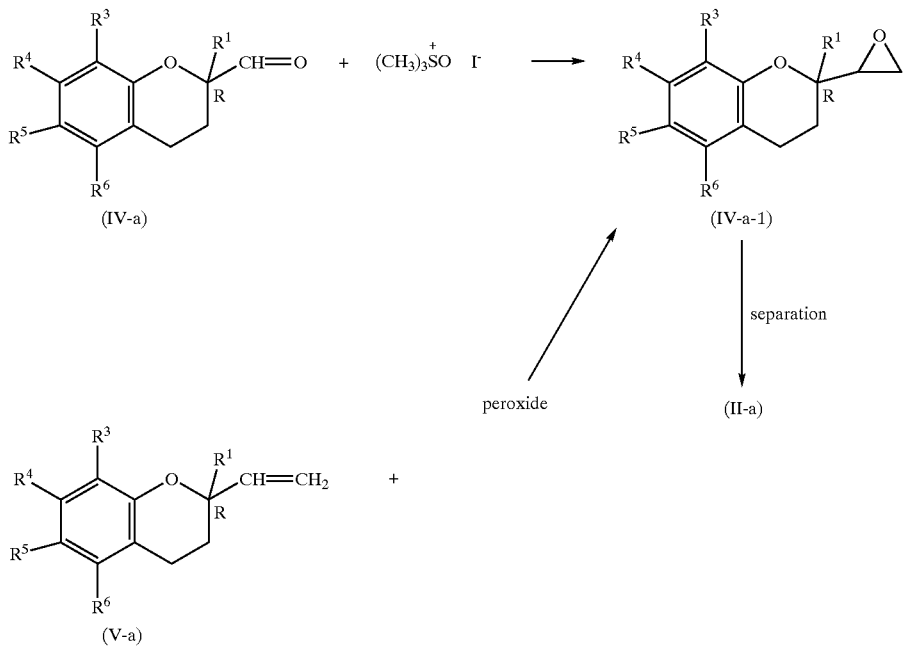

The compounds of formula (IV-a), (IV-b), (V-a) or (V-b) are obtained by a suitable separation procedure, i.e. by HPLC, or by a reduction reaction of the corresponding optically active racemic acids whereas (IV-a) or (IV-b) can be converted to (V-a) or (V-b) by a Wittig reaction. The said corresponding optically active acids in turn can be obtained by conventional separation techniques, i.e. by salt or amide formation with an optically active reagent and a selective crystallization procedure or a HPLC separation.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propane-tricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Conversely, the salt form can be converted by treatment with alkali into the free base form.

3,337,628 and 3,520,919, in particular propranolol; U.S. Pat. No. 3,873,600, in particular metoprolol; U.S. Pat. No. 3,511,836, in particular prazosin; U.S. Pat. No. 2,484,029, in particular hydralazine; U.S. Pat. No. 2,928,829 in particular guanethidine; U.S. Pat. No. 2,503,059, in particular phentolamine; U.S. Pat. No. 3,261,859, in particular verapamil; U.S. Pat. No. 3,485,847 in particular nifedipine; U.S. Pat. No. 3,910,924, in particular carteolol; German Pat. Nos. 2,458,624 and 2,458,625, in particular celiprolol. A particular group of blood pressure reducing compounds are the compounds of U.S. Pat. No. 4,654,362 other than the compounds of formula (I) and in particular the enantiomers of the compounds of formula (I), i.e. the SRRR-isomers. A particular compound is [2S,αR,2'R,α'R]-α,α'-[iminobismethylene]bis[6-fluoro-3,4-dihydro-2H-1-benzopyran-2-methanol. These groups of active ingredients are listed with the purpose of providing representative examples but not with the purpose of restricting the scope of the present invention. The said SRRR isomers and the said particular compound can be prepared following the same procedures as previously described for the preparation of the compounds of formula (I), but starting from the enantiomers of the intermediates (II-a), (III-a), (II-b) and (III-b). The latter enantiomers in turn can be obtained as described hereinabove for the preparation of (II-a), (III-a), (II-b) and (III-b), but starting from the enantiomers of (IV-a) or (V-a) and isolating the appropriate stereoisomers in stereochemical separation procedures. The enantiomers of (IV-a) and (V-a) in the same way can be obtained as described for the preparation of (IV-a) and (V-a) starting from the appropriate enantiomeric starting materials and/or isolating the appropriate stereoisomers in stereochemical separations.

The compounds of formula (I) and the acid addition salts thereof may be administered before, during or after the administration of the blood pressure reducing agent provided that the time of the administration of the compounds of formula (I) in relation to the administration of the blood pressure reducing agent allows the compound of formula (I) to be effective in potentiating the effects of the blood pressure reducing agent. Preferably the compound of formula (I) and the blood pressure reducing agent are administered in the form of suitable compositions. Said compositions are meant to also comprise products containing a compound of formula (I) as defined hereinabove and a blood-pressure reducing agent as a combined preparation for simultaneous, separate or sequential use in blood-pressure reducing therapy. Such products may for example comprise a kit comprising a container with a suitable composition containing a compound of formula (I) and another container containing a composition with a blood pressure reducing agent. Such product may have the advantage that the physician wishing to administer blood pressure reducing therapy can select, based on the diagnosis of the patient to be treated, the appropriate amounts of both components and the sequence of administration.

When administered during the administration of the blood pressure reducing agent, a composition containing both the blood pressure reducing agent and the active ingredient of formula (I) may particularly be convenient.

In a further aspect of the present invention there is provided a composition comprising an amount capable of potentiating the effects of blood pressure reducing agents of a compound of formula (I) as defined hereinabove and a blood pressure reducing agent. In the said composition, the molar ratio between the compound of formula (I) and the blood pressure reducing agent may be other than 1:1, but in particular may be 1:1. The amount of the active ingredient of formula (I) in such composition will be so that a potentiating effect on the effects of the blood-pressure reducing agent is obtained; the amount of the blood pressure reducing agent will be so that when potentiated, a blood pressure reducing effect is obtained upon administration. In particular, it is contemplated that the molar ratio of the compound of formula (I) to the blood pressure reducing compound may be situated between 50:1 and 1:50, in particular between 20:1 and 1:20, or between 10:1 and 1:10, or between 5:1 and 1:5, more particularly between 2:1 and 1:2. Particular such compositions are those wherein the blood pressure reducing agent is one of the agents pertaining to the patents cited hereinabove, and more particularly the agents specifically mentioned hereinabove.

The present invention also provides a composition comprising a pharmaceutically acceptable carrier and as active ingredient an amount capable of potentiating the effects of blood pressure reducing agents of a novel compound of formula (I) or a pharmaceutically acceptable acid-addition salt thereof, as defined hereinabove.

To prepare such pharmaceutical compositions, an effective amount of the particular compound or compounds, in base or acid-addition salt form, as the active ingredient or active ingredients is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention also concerns a method of potentiating the effects of blood pressure reducing agents in warm-blooded animals in need of blood pressure reducing medication, said method comprising administering to said warm-blooded animals of an effective amount of a blood pressure reducing agent and a compound of formula (I) as defined hereinabove.

Or alternatively, the present invention concerns a method of lowering the blood pressure in warm-blooded animals suffering therefrom, said method comprising administering to said warm-blooded animals of an effective amount of a blood pressure reducing agent and a compound of formula (I) as defined hereinabove.

Those of skill in treating subjects suffering from an increased blood pressure could easily determine the effective amount from the test results presented hereinafter. In general it is contemplated that an effective daily dose of the compounds of formula (I) or their pharmaceutically acceptable acid-addition salts would be from 0.01 mg/kg to 50 mg/kg body weight, in particular from 0.1 mg/kg to 10 mg/kg body weight and preferably from 0.1 mg/kg to 1 mg/kg body weight.

All above cited references are incorporated herein by reference.

The following examples are intended to illustrate and not to limit the scope of the present invention in all its aspects. Unless otherwise stated all parts therein are by weight.

Whenever used in the following examples "A" refers to the isomer which was first isolated and "B" to the one which was subsequently isolated.

Experimental Part

A. Preparation of the Intermediates

EXAMPLE 1 a) A mixture of 63.4 parts of 6-fluoro-4-oxo-4H-1-benzopyran-2-carboxylic acid and 400 parts of acetic acid was hydrogenated at normal pressure and at room temperature with 3 parts of palladium-on-charcoal catalyst 10%. After the calculated amount of hydrogen was taken up, the catalyst was filtered off and the filtrate was evaporated. The residue was stirred in petroleumether. The product was filtered off and dried in vacuo at 70° C., yielding 49 parts (83%) of 6-fluoro-3,4-dihydro-2H-1-benzopyran-2-carboxylic acid (int. 1).

b) To a stirred solution of 9.75 parts of intermediate 1 in 90 parts of methylbenzene were added 16 parts of thionyl chloride. The mixture was stirred for 2 hours at 60° C. The reaction mixture was evaporated. The residue was taken up twice in 45 parts of methylbenzene and the latter was evaporated each time. The residue was taken up in 90 parts of methylbenzene. There were added first 10.5 parts of N,N-diethylethanamine and then a solution of 14.25 parts of (+)-1,2,3,4,4a,9,10,10a-octa-hydro-1,4a-dimethyl-7-(1-methylethyl)-1-phenanthrenemethanamine [(+)-dehydroabiethylamine] in 45 parts of methylbenzene. After stirring for 2 hours, the organic layer was washed successively with water, a sodium hydroxide solution 10%, a hydrochloric acid solution 10% and water, dried, filtered and evaporated. The residue was taken up in 120 parts of warm ethanol. The product was filtered off and crystallized from ethanol, yielding 6.6 parts (28.4%) of (A)-6-fluoro-3,4-dihydro-N-[dehydroabiethyl]-2H-1-benzopyran-2-carboxamide (int. 2).

c) A mixture of 6.8 parts of intermediate 2, 75 parts of acetic acid and 36 parts of concentrated hydrochloric acid was stirred for 24 hours at reflux temperature. After cooling, the reaction mixture was poured into water. The product was extracted with 1,1'-oxybisethane. The extract was washed twice with water, dried, filtered and evaporated. The residue was taken up in 1,1'-oxybisethane. 5 Parts of a sodium hydroxide solution were added. The product was filtered off, taken up in trichloromethane and treated with 50 parts of a hydrochloric acid solution 10%. The organic layer was dried, filtered and evaporated, yielding 1.1 parts of (+)-(S)-6-fluoro-3,4-dihydro-2H-1-benzopyran-2-carboxylic acid; mp. 99.7° C. $[\alpha]_D^{25}$=+14.88° (c=1% in DMF) (int. 3).

d) To a stirred solution of 22.5 parts of intermediate 3 in 180 parts of tetrahydrofuran were added 18.7 parts of 1,1'-carbonylbis[1H-imidazole]. The whole was stirred for 1 hour at room temperature and cooled to −70° C. 136 Parts of a 25% solution of [bis(2-methylpropyl)]aluminum hydride in methylbenzene were added dropwise during a period of 20 minutes. Upon completion, stirring was continued for 20 minutes at −70° C. 40 Parts of methanol were added and the mixture was poured into water. The product was extracted with 1,1'-oxybisethane. The extract was washed successively with a hydrochloric acid solution 10%, water and a sodium hydrogen carbonate solution, dried, filtered and evaporated, yielding 12 parts (57.9%) of (+)-(S)-6-fluoro-3,4-dihydro-2H-1-benzopyran-2-carboxaldehyde as an oily residue (int. 4).

e) 6.3 Parts of a sodium hydride dispersion 50% were washed twice with petroleum ether and then taken up in 250 parts of dimethyl sulfoxide. 29 Parts of trimethylsulfoxonium iodide were added during a period of 30 minutes and stirring was continued for 20 minutes. A solution of 12 parts of intermediate 4 in 10 parts of dimethyl sulfoxide was added dropwise and upon completion, the mixture was stirred for 30 minutes. The reaction mixture was poured into water and the product was extracted with 1,1'-oxybisethane. The extract was washed three times with water, dried, filtered and evaporated. The residue was purified by column chromatography (HPLC) over silica gel using a mixture of methylbenzene and ethyl acetate (90:10 by volume) as eluent. The pure fractions were collected and the eluent was evaporated, yielding 2.1 parts (9.8%) of (+)-[S(S)]-6-fluoro-3,4-dihydro-2-oxiranyl-2H-1-benzopyran as an oily residue (int. 5).

EXAMPLE 2 a) In the procedure described hereinabove in example 1b) 6.1 parts (26.3%) of the compound (B)-6-fluoro-3,4-dihydro-N-[dehydroabiethyl]-2H-1-benzopyran-2-carboxamide (int. 6) was obtained as a residue.

b) A mixture of 6.1 parts of intermediate 6, 75 parts of acetic acid and 36 parts of concentrated hydrochloric acid was stirred for 24 hours at reflux temperature. The reaction mixture was poured into water. The product was extracted with 1,1'-oxybisethane. The extract was washed twice with water, dried, filtered and evaporated in vacuo. The residue was crystallized from petroleum ether. The product was filtered off and dried, yielding 0.9 parts of (−)-(R)-6-fluoro-3,4-dihydro-2H-1-benzopyran-2-carboxylic acid; mp. 102.5° C. $[\alpha]_D^{25}$=−13.39° (c=1% in DMF) (int. 7).

c) To a stirred and refluxed solution of 36 parts of intermediate 7 in 400 parts of methanol were added 1.8 parts of sulfuric acid. The mixture was further and refluxed for 4 hours. After cooling, the reaction mixture was evaporated. The residue was taken up in 1,1'-oxybisethane. The mixture was washed successivily twice with a sodium hydrogen carbonate solution and once with water, dried, filtered and evaporated, yielding 33 parts (82.6%) of (−)-(R)-methyl 6-fluoro-3,4-dihydro-2H-1-benzopyran-2-carboxylate as an oily residue (int. 8).

d) To a stirred and cooled (−80° C.) solution of 33 parts of intermediate 8 in 450 parts of methylbenzene were added dropwise 255 parts of a solution of [bis(2-methylpropyl)] aluminium hydride in methylbenzene under nitrogen atmosphere. Stirring was continued for 30 minutes at −80° C. 16 Parts of methanol were added and the reaction mixture was poured into water. The mixture was acidified with hydrochloric acid and the two layers were separated. The organic phase was dried, filtered and evaporated, yielding an oily residue of 32 parts (the residue was set aside). 9.6 Parts of a sodium hydride dispersion 50% were washed first three times with petroleumether and then taken up in 500 parts of dimethyl sulfoxide. 44 parts of trimethylsulfoxonium iodide were added portionwise and after complete addition, the whole was stirred for 20 minutes at room temperature. To the thus obtained mixture was added dropwise a solution of 32 parts of the oily residue, which was set aside (see above), in 20 parts of dimethyl sulfoxide. Upon completion, stirring was continued for 20 minutes at room temperature. The whole was poured into water and the product was extracted with 2,2'-oxybispropane. The extract was dried, filtered and evaporated. The residue was separated by column chromatography (HPLC) over silica gel using a mixture of hexane and ethyl acetate (80:20 by volume) as eluent. The desired fractions were collected and the eluent was evaporated, yielding 8.2 parts (24.8%) of (−)-[R(S)]-6-fluoro-3,4-dihydro-2-oxiranyl-2H-1-benzopyran as a residue (int. 9).

e) A solution of 8.2 parts of intermediate 9 and 20 parts of benzenemethanamine in 80 parts of methanol was stirred overnight at room temperature. The reaction mixture was evaporated and the residue was taken up in 2,2'-oxybispropane. The precipitated product was filtered off and crystallized from acetonitrile. The product was filtered off and dried, yielding 4.6 parts (38.1%) of (−)-[R(S)]-6-fluoro-3,4-dihydro-α-[[(phenylmethyl)amino]methyl]-2H-1-benzopyran-2-methanol (int. 10).

B. Preparation of the Final Compounds

EXAMPLE 3 a) A solution of 1.8 parts of intermediate 5 and 2 parts of intermediate 10 in 40 parts of ethanol was stirred for 4 hours at reflux temperature. The reaction mixture was evaporated, yielding 3.5 parts (100%) of [2R,αS,2'S,α'S]-α,α'-[[(phenylmethyl)imino]bismethylene]bis[6-fluoro-3,4-dihydro-2H-1-benzopyran-2-methanol] as a residue (int. 11).

b) A mixture of 3.5 parts of intermediate 11 and 250 parts of 2-methoxyethanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was taken up in trichloromethane and purified by column chromatography over silica gel using trichloromethane as eluent. The pure fractions were collected and the eluent was evaporated. The residue was crystallized twice from acetonitrile. The product was filtered off and dried, yielding 1.2 parts (42%) of [2R,αS,2'S,α'S]-α,α'-iminobismethylene]bis[6-fluoro-3,4-dihydro-2H-1-benzopyran-2-methanol]; mp. 142.7° C. (compound 1).

EXAMPLE 4

A mixture of 19.4 parts of (RS,SS)-α,α'-[[(phenylmethyl)imino]bis(methylene)bis[3,4-dihydro-2H-1-benzopyran-2-methanol], prepared as described in U.S. Pat. No. 4,654,362 (see compound 16 in the experimental part of the latter; the designation "A⁻B⁺" referring to the RSSS isomer) and 243 parts of 2-methoxyethanol was hydrogenated at normal pressure and at room temperature with 2 parts of palladium-on-charcoal catalyst 10%. After the calculated amount of hydrogen was taken up, the reaction mixture was filtered over diatomaceous earth and evaporated. The residue was crystallized twice from acetonitrile, yielding 6.8 parts (43.8%) of (RS,SS)-α,α'-[iminobis(methylene)]]bis[3,4-dihydro-2H-1-benzopyran-2-methanol]; mp. 136.1° C. (compound 2).

EXAMPLE 5

A mixture of 6 parts of intermediate 10, 5 parts of (SS)-3,4-dihydro-2-oxiranyl-2H-1-benzopyran, prepared as described in example 17 of U.S. Pat. No. 4,654,362 (intermediate 53, the designation "B⁺" referring to the SS-isomer) and 119 parts of ethanol was refluxed for 18 hours. The reaction mixture was evaporated and the residue was added to 275 parts of 2-methoxyethanol and hydrogenated at normal pressure and at room temperature with 2 parts of palladium-on-charcoal catalyst 10%. After the calculated amount of hydrogen was taken up, the catalyst was filtered off and the filtrate was evaporated. The residue was crystallized from acetonitrile, yielding 3.8 parts (49.3%) of (RSSS)-α-[[[2-(3,4-dihydro-2H-1-benzopyran-2-yl)-2-hydroxyethyl]amino]methyl]-6-fluoro-3,4-dihydro-2H-1-benzopyran-2-methanol; mp. 154.2° C. (compound 3).

EXAMPLE 6

Following the same procedures as described in example 5 and starting from (SS)-6-fluoro-3,4-dihydro-α-[[(phenylmethyl)amino]methyl]-2H-1-benzopyran-2-methanol (obtained from the reaction of intermediate 5 with benzenemethanamine) and (SR)-3,4-dihydro-2-oxiranyl-2H-1-benzopyran (obtained as described in example 17, compound 52 of U.S. Pat. No. 4,654,362; the designation "A⁻" referring to the SR isomer) there was also prepared (SSSR)-α-[[[2-(3,4-dihydro-2H-1-benzopyran-2-yl)-2-hydroxyethyl]amino]-methyl]-6-fluoro-3,4-dihydro-2H-1-benzopyran-2-methanol; mp. 140.7° C. (compound 4).

C. Pharmacological Examples

Adult spontaneous hypertensive rats (6 months of age) were anesthetized by ether inhalation. The femoral artery was dissected and cannulated, and the catheter was connected to a strain-gauge blood pressure transducer. When the animals were fully awake, they were restrained and the systolic and diastolic arterial blood pressure were continuously recorded. An observation period of at least 30 min preceded the administration of the test compound. All test compounds were dissolved in 20% polypropylene glycol and injected intraperitoneally. After administration of the test drug the systolic and diastolic arterial blood pressure and the heart rate were recorded during a period of 120 minutes. The average blood pressure and heart rate was calculated from the results obtained at various time intervals after administration of the test drug. The following table illustrates the difference between treated and untreated animals expressed as a percentage (Δ%) in the systolic and diastolic blood pressure and the heart rate.

Δ% Changes (average 120 min) in systolic and diastolic (SBP, DBP) and in heart rate (HR) in spontaneous hypertensive rats

|  | *<br>1.25 mpk | Hydralazine<br>0.63 mpk | Guanethidine<br>2.5 mpk | Phentolamine<br>0.63 mpk |
|---|---|---|---|---|
| SBP | 0 | −7.5 | −9.3 | −9.85 |
| DBP | +2.1 | −9.9 | −6.2 | −13.1 |
| HR | 0.5 | −1.45 | −7.9 | +5.1 |

|  | Hydralazine<br>0.63 mpk + *<br>1.25 | Guanethidine<br>2.5 mpk + *<br>1.25 | Phentolamine<br>0.63 mpk + *<br>1.25 |
|---|---|---|---|
| SBP | −20.9 | −15.7 | −16.7 |

-continued

| | | | | |
|---|---|---|---|---|
| DBP | −28 | | −16.7 | −21.2 |
| HR | −3.6 | | −17.6 | +0.9 |

| | * 2.5 mpk | Atenolol 10 mpk | Propranolol 5 mpk | Metoprolol 10 mpk | Prazosin 0.01 mpk |
|---|---|---|---|---|---|
| SBP | −7 | −3.7 | −2 | −1.2 | −10.9 |
| DBP | 0 | +5.9 | +12.4 | +12.8 | −11.3 |
| HR | 0 | −28.1 | −20.7 | −16.6 | +1.6 |

| | Atenolol 10 mpk + * 2.5 | Propranolol 5 mpk + * 2.5 | Metoprolol 10 mpk + * 2.5 | Prazosin 0.01 mpk + * 2.5 |
|---|---|---|---|---|
| SBP | −21 | −9.6 | −12.7 | −27.6 |
| DBP | −21 | +3.2 | −4 | −28.7 |
| HR | −32 | −33.1 | −28.25 | −6.8 |

* = [2R,αS,2'S,α'S]-α,α'-[iminobismethylene]bis[6-fluoro-3,4-dihydro-2H-1-benzopyran-2-methanol]. (compound 1).

What is claimed is:

1. A composition consisting of the compound [2R,αS,2'S, α'S]-α,α'-[iminobismethylene]bis[6-fluoro-3,4-dihydro-2H-1-benzopyran-2-methanol] having the formula:

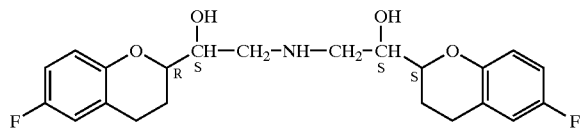

or a pharmaceutically acceptable acid addition salt thereof.

2. A pharmaceutical composition consisting of a pharmaceutically acceptable carrier and, as active ingredients:

(a) the blood pressure reducing compound [2S,αR, 2'R, α'R]-α,α'-[iminobismethylene]bis[6-fluoro-3,4-dihydro-2H-1-benzopyran-2-methanol] having the formula:

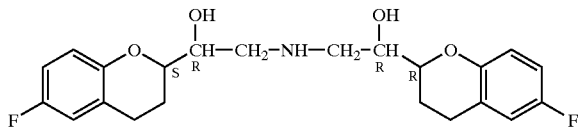

or a pharmaceutically acceptable acid addition salt thereof; and (b) the compound [2R,αS,2'S,α'S]-α,α'-[iminobismethylene]bis[6-fluoro-3,4-dihydro-2H-1-benzopyran-2-methanol] having the formula:

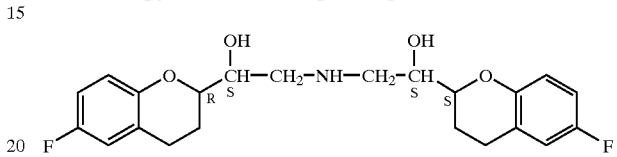

or a pharmaceutically acceptable acid addition salt thereof.

3. A composition according to claim 2 wherein compound (b) is present in an amount capable of potentiating the activity of the blood pressure reducing compound (a).

4. A composition according to claim 3 wherein the molar ratio of the compounds (a) and (b) is about 1:1.

5. A method of treating hypertension in warm blooded animals in need of such treatment which comprises administering to said warm blooded animals an effective amount of the pharmaceutical composition of claim 2.

6. A method of treating hypertension in warm blooded animals in need of such treatment which comprises administering to said warm blooded animals an effective amount of the pharmaceutical composition of claim 4.

* * * * *

(12) EX PARTE REEXAMINATION CERTIFICATE (6664th)
United States Patent
Xhonneux et al.

(10) Number: US 6,545,040 C1
(45) Certificate Issued: Feb. 17, 2009

(54) METHOD OF LOWERING THE BLOOD PRESSURE

(75) Inventors: Raymond Mathieu Xhonneux, Vlimmeren (BE); Guy Rosalia Eugène Van Lommen, Berlaar (BE)

(73) Assignee: Janssen Pharmaceutica N.V.

Reexamination Request:
No. 90/008,356, Jan. 26, 2007

Reexamination Certificate for:
Patent No.: 6,545,040
Issued: Apr. 8, 2003
Appl. No.: 07/825,488
Filed: Jan. 24, 1992

Related U.S. Application Data

(63) Continuation of application No. 07/325,181, filed on Mar. 16, 1989, now abandoned, which is a continuation-in-part of application No. 07/172,747, filed on Mar. 23, 1988, now abandoned.

(51) Int. Cl.
*A61K 31/35* (2006.01)
*C07D 311/58* (2006.01)
*C07D 311/00* (2006.01)

(52) U.S. Cl. ................ 514/451; 514/452; 514/602
(58) Field of Classification Search ................ None
See application file for complete search history.

(56) References Cited

U.S. PATENT DOCUMENTS

| | | | |
|---|---|---|---|
| 2,484,029 A | 10/1949 | Hartmann et al. | 544/237 |
| 2,503,059 A | 4/1950 | Miescher et al. | 548/348.1 |
| 2,928,829 A | 3/1960 | Mull et al. | 540/483 |
| 3,261,859 A | 6/1966 | Dengel et al. | 558/390 |
| 3,337,628 A | 8/1967 | Crowther et al. | 564/349 |
| 3,485,847 A | 12/1969 | Bossert et al. | 546/321 |
| 3,511,836 A | 5/1970 | Hess et al. | 544/291 |
| 3,520,919 A | 7/1970 | Crowther et al. | 560/107 |
| 3,663,607 A | 5/1972 | Barrett et al. | 562/467 |
| 3,836,671 A | 9/1974 | Barrett et al. | 514/620 |
| 3,873,600 A | 3/1975 | Brandstrom et al. | 560/29 |
| 3,910,924 A | 10/1975 | Tamura et al. | 546/158 |
| 3,983,169 A | 9/1976 | Zolss et al. | 562/595 |
| 4,034,009 A | 7/1977 | Zolss et al. | 564/51 |
| 4,313,955 A | 2/1982 | Huebner et al. | 514/452 |
| 4,380,635 A | 4/1983 | Peters | 546/202 |
| 5,256,687 A | 10/1993 | Becker et al. | 514/419 |

FOREIGN PATENT DOCUMENTS

| | | |
|---|---|---|
| DE | 2 458 624 | 7/1975 |
| DE | 2 458 625 | 7/1975 |
| EP | 0 050 585 | 4/1982 |
| EP | 0 145 067 | 6/1985 |
| EP | 0 215 357 A2 | 3/1987 |
| EP | 0 334 429 B1 | 11/1992 |
| GB | 1 054 655 | 1/1967 |

OTHER PUBLICATIONS

Peeters et al. ("Structure and Absolute Configuration of Nebivolol: (+/−)−(R*{S*[S*−(S)]}−α,'−α[Iminobis(methylene)]bis[6−fluoro−3, 4−dihydro−2H−1−benzopyran−2−methanol) (Nebivolol) Hydrochloride (I) and (+)−(S{R[R−(R)]})−Nebivolol Hydrobromide Dihydrate (II)" Acta. Cryst. C49, pp. 2154–2157, 1993).*

De Crée et al., "Subacute Hemodynamic Effects of Nebivolol in Man at Rest and During Exercise," *Angiology*, Jun. 1987, 38(6), 440–448.

De Crée et al., "Haemodynamic Effects in Man During Exercise of a Single Oral Does of Narbivolol (R 67555), a New Beta–1–Adrenoceptor Blocking Agent: A Comparative Study with Atenolol, Pindolol, and Propranolol," *Drug Dev Res*, 1986, 8, 109–117.

De Crée et al., "Hemodynamic Effects in Men of Nebivolol, A Chemically Novel Selective Beta–1 Adrenoceptor Blocking Drug, Comparing the Results of Systolic Time Intervals with Radionuclide Andgiocardigraphy," *34th Annual Meeting of the American College of Angiology, Paradise Island (Bahamas)*, Oct. 18–23, 1987, abstract.

De Crée et al., "Hemodymanic Effects of Nebivolol in Men: Comparison of Radionuclide Angiocardiography with Systolic Time Intervals," *Angiology*, Jun. 1988, 39(6), 526–534.

Woestenborghs et al., "HPLC Fluorescence Method for the Determination of the New $\beta_1$–Adrenoreceptor Blocking Agent Nebivolol in Human Plasma," *Methodological Surveys in Biochemistry and Analysis: Bioanalysis of Drugs and Metabolites, Especially Anti–Inflammatory and Cardiovascular*, Reid et al. (eds.), Sep. 1988, 215–216.

Yagel, S. et al., "Effects of the Novel $Beta_1$–Selective Adrenoreceptor Antagonist, Nebivolol, On Myocardial Oxygen Supply and Demand in the Anesthesized, Open Chest Dog," Department of Biological Research, The Janssen Research Foundation and McNeil Pharmaceutical, 1987, *Hemodynamic Section*, 3.

Ariëns, E., "Stereochemistry: A Source of Problems in Medicinal Chemistry," *Medicinal Research Reviews*, 1986, 6(4), 451–466.

Ariëns, E.J., "Chirality in Bioactive Agents and its Pitfalls," *TIPS*, May 1986, 200–205.

Ariëns, E.J., "Stereochemistry, a Basis for Sophisticated Nonsense in Pharmocokinetics and Clinical Pharmacology," *European Journal of Clinical Pharmacology*, 1984, 26, 663–668.

"International Nonproprietary Names for Pharmaceutical Substances," Supplement to *WHO Chronicle*, 1986, 40(5), 1–21.

McNeely, W. et al., "Nebivolol in the Management of Essential Hypertension," *Drugs*, 1999, 57(4), 633–651.

"Nebilet Tablets 5mg," http://home.intekom.com/pharm/adcock/nebilet.html, Mar. 20, 2006, 4 pages.

Nebilet®, "Nebilet Tabletten," Rote Liste Win®, Mar. 20, 2006, 1 page.

(Continued)

*Primary Examiner*—Dwayne C Jones

(57) ABSTRACT

A method of potentiating the effects of blood pressure reducing agents in warm-blooded animals, said method comprising administering to said warm-blooded animals of an effective amount of a blood pressure reducing agent and a 2,2'-iminobisethanol derivative.

OTHER PUBLICATIONS

Van de Water et al., "Pharmacological and Hemodynamic Profile of Nebivolol, a Chemically Novel, Potent, and Selective $\beta_1$-Andrenergic Antagonist," *J. Cardiovascular Pharmacology*, May 1988, 11(5), 552–563.

"International Nonproprietary Names for Pharmaceutical Substances (INN)," *WHO Drug Information*, 1995, 9(3), 1–28.

Van de Water, A. et al., "Cardiovascular effects of dl–nebivolol and its enantiomers—a comparison with those of atenolol," *European Journal of Pharmacology*, 1988, 156, 95–103.

Report entitled: "Hemodynamic effects of Nebivolol in Men: Comparison of Radionuclide Angiocardiography with Systolic Time Intervals," *Angiology*, Oct. 1987, 39(6), 526–534.

Siebert, C. D., "Stereochemistry of Beta–blockers. Spatial examination and description of nebivolol," Pharm. Unserer Zeit, 2004, Nr. 6. Both original and English translation, 15 pages.

Mutschler, E., Arzneimittel Wirkungen (1981), pp. 419–425, WVG, Stuttgart (English translation only).

De Cree, J. et al., "A survey of 15 years experience with systolic time intervals," Acta Antwerpiensia, 4, 1987, 2–18, (JA2).

Vandeplassche, G. et al., "Beta–Blockade in the Ischemic Reperfused Working Rabbit Heart: Dissociation of Beta–Adrenergic Blocking and Protective Effects," Arch. Int. Pharmacodyn., 1989, 301, 165–181 (JA8).

Denmark, S. E., "Enantioselective Ring Opening of Epoxides with Silicon Tetrachloride in the Presence of a Chiral Lewis Base: Mechanism Studies," Adv. Synth. Catal., 2007, 349, 567–582.

Brandes, B. and et al., "Regioselective Ring Opening of Enantiomerically Enriched Epoxides via Catalysis with Chiral (Salen)Cr(III) Complexes," Synlett, 2001, SI, 1013–1015.

Van Gaetel, S. et al., "Thirty–Three Years of Drug Discovery and Research With Dr. Paul Janssen," Drug Development Research, 1986, 8, 1–13.

Ruffolo, Jr., R. R., "Stereoselectivity in Adrenergic Agonists and Adrenergic Blocking Agents," in "Stereochemistry and Biological Activity of Drugs,", Arens, E.J. et al., (Eds.), 1983, Blackwell Scientific Publications Oxford, pp. 103–125.

Gold, E. H. et al., "Synthesis and Comparison of Some Cardiovascular Properties of the Stereoisomers of Labetalol," J. Med. Chem., 1982, 25, pp. 1363–1370.

Ruf, G. et al., "Determination of the anti–ischemic activity of nevivolol in comparison with atenolol," Int. J. Cardiol., 1994, 43, 279–285.

"Biochemistry" (Ed.: D. Voet, J. G. Voet), 3rd Ed., 2004, John Wiley & Sons, Inc. New York, pp. 75 to 76.

"Enzymes in Synthetic Organic Chemistry" (Ed: C.H. Wong and G.M. Whitesides), 1994, Pergamon Press, Elsevier, Oxford 1994, pp. v to xi.

Ruf, G. et al., "Determination of the anti–ischemic activity of nebivolol in comparison with atenolol," Int. J. Cardiol., 1994, 43, pp. 279–285.

Maier, N.M. and Lindner, W., "Stereoselective Chromatographic Methods for Drug Analysis" in "Chirality in Drug Research" (Ed.: E. Francotte and W. Lindner), 2006, Wiley–VCH Verlag GmbH & Co KGaA, Weinheim, pp. 189–260.

"Stereoselective Synthesis" (Ed. M. Nogradi), 2nd. Ed., 1995, VCH Verlagsgesellschaft mbH, Weinheim, pp. XI to XV.

Brunner, H., "Enantioselective Synthesis with Optically Active Transition–Metal Catalysts," Synthesis, 1988, pp. 645–654.

"Asymmetric Catalysis In Organic Synthesis" (Ed.: R. Noyori), 1994, John Wiley & Sons, Inc., New York, pp. vii to xi.

* cited by examiner

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

* * * * *